United States Patent [19]
Sato et al.

[11] Patent Number: 4,866,044
[45] Date of Patent: Sep. 12, 1989

[54] SOLUBILIZED COMPOSITION OF POORLY-SOLUBLE PHARMACEUTICAL PRODUCT

[75] Inventors: Jun Sato, Hyogo; Katsumi Matsuzaki; Yoshiharu Matsukura, both of Nara, all of Japan

[73] Assignee: Takeda Chemical Industries, Ltd., Osaka, Japan

[21] Appl. No.: 881,795

[22] Filed: Jul. 3, 1986

[30] Foreign Application Priority Data

Jul. 9, 1985 [JP] Japan ................... 60-151680

[51] Int. Cl.$^4$ .................... A61K 31/685; A61K 47/00
[52] U.S. Cl. ......................... 514/77; 514/78; 514/784; 514/970; 514/975
[58] Field of Search .............. 514/77, 163–165, 514/182, 784, 970, 975; 260/397.1

[56] References Cited

U.S. PATENT DOCUMENTS

| | | | |
|---|---|---|---|
| 3,197,368 | 7/1965 | Lappe et al. | 514/78 |
| 4,408,052 | 10/1983 | Hozumi et al. | 546/22 |
| 4,582,824 | 4/1986 | Nishikawa et al. | 514/77 |
| 4,681,876 | 7/1987 | Marples et al. | 514/182 |

FOREIGN PATENT DOCUMENTS

1062390 2/1957 Fed. Rep. of Germany.
2022898 11/1970 Fed. Rep. of Germany.

*Primary Examiner*—Douglas W. Robinson
*Assistant Examiner*—Raymond J. Henley, III
*Attorney, Agent, or Firm*—Wegner & Bretschneider

[57] ABSTRACT

3-(n-Octadecylcarbamoyloxy)-2-methoxypropyl 2-thiazolioethyl phosphate solubilized with use of a salt of salicyclic acid or/and a salt of a bile acid can be administered by stable injection without causing precipitation. A composition containing a reducing sulfur compound or a sequestering agent besides the above mentioned ingredients can be stored for a long term even at room temperature as well as a cold place.

7 Claims, No Drawings

SOLUBILIZED COMPOSITION OF POORLY-SOLUBLE PHARMACEUTICAL PRODUCT

INDUSTRIAL FIELD OF UTILIZATION

This invention relates to solubilized compositions of a poorly-soluble pharmaceutical product.

PRIOR ART 3-(n-Octadecylcarbamoyloxy)-2-methoxypropyl 2-thiazolioethyl phosphate:

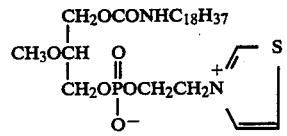
[1]

has been known to show actions of inhibiting platelet activating factor (PAF) and of preventing endotoxin shock, more specifically, to strongly inhibit platelet aggregation, shock symptoms (e.g. hypotension, lethal effect, etc.) and allergic reaction. Therefore, the compound [1] can be used for prophylaxis and therapy of shocks such as endotoxin shock, disseminated intravascular coagulation, diseases such as anaphylactic shock and allergic bronchial asthma. When the compound [1] is used for prophylaxis and therapy of shocks, it is usually administered by intravenous injection in a dosage of usually about 50–500 mg for an adult.

PROBLEMS THAT THE INVENTION IS DESIGNED TO SOLVE

The present inventors found that, although the compound [1] shows a solubility of about 100 mg/ml in water at 50°–60° C., as shown in Table 1, the compound [1] once dissolved precipitates out as the time elapses below room temperature, and the solution becomes a suspension.

TABLE 1

| Time (h) | (15° C.) Compound [1] 10 mg/ml | 50 mg/ml |
| --- | --- | --- |
| 0 | − | − |
| 0.5 | + | + |
| 1 | + | + |
| 3 | + | + |
| 5 | + | + |

−: clear
+: cloudy

Therefore, in order to administer the compound [1], it is required to administer it immediately after prepared of its injectable solution or to use an extremely diluted solution. In the former case, however, the solution prepared in a dispensing room tends to become a suspension before administration, while, in the latter case, the volume of the injectable solution becomes too great, thus being very disadvantageous from the view point of formulation of injectable preparations.

The present inventors conducted extensive studies for increasing the solubility of the compound [1] at room temperature (around 25° C.) and about 5° C. (guaranteeing the use in cold districts), and found that specific substances serve to specifically solubilize the compound [1] in water, and further studies for preparation of injectable freezedried preparations storable for a long period of time at room temperature to reach the completion of the present invention.

MEANS OF SOLVING THE PROBLEMS

The present invention provides (1) a method of solubilizing 3-(n-octadecylcarbamoyloxy)-2-methoxypropyl 2-thiazolioethyl phosphate in water, characterized by using a salt of salicylic acid or/and a salt of a bile acid, (2) a composition containing ① 3-(n-octadecylcarbamoyloxy)-2-methoxypropyl 2-thiazolioethyl phosphate and ② a salt of salicylic acid or/and a salt of a bile acid, (3) a method of preparing a stable composition, characterized by solubilizing 3-(n-octadecylcarbamoyloxy)-2-methoxypropyl 2-thiazolioethyl phosphate in water with use of a salt of salicylic acid or a salt of a bile acid, followed by adding a reducing sulfur compound or a sequestering agent, and (4) a stable composition containing ① 3-(n-octadecylcarbamoyloxy)-2-methoxypropyl 2-thiazolioethyl phosphate, ② a salt of salicylic acid or a salt of a bile acid and ③ a reducing sulfur compound or a sequestering agent.

The salts of salicylic acid employable in the present invention are exemplified by alkali metal salts of salicylic acid, such as sodium salicylate and potassium salicylate, and, among them, sodium salicylate is preferable.

The salts of bile acids are exemplified by alkali metal (e.g. sodium, potassium) salts of cholic acid, glycocholic acid, taurocholic acid, tauroglycocholic acid, cholanic acid, lithocholic acid, deoxycholic acid, dehydrocholic acid, chenodesoxycholic acid, etc. and among them sodium salts thereof are preferable and sodium deoxycholate is the most preferable.

The reducing sulfur compounds are exemplified by glutathione, alkali metal metabisulfite (e.g. sodium metabisulfite, potassium metabisulfite), alkali metal sulfite (e.g. sodium sulfite, potassium sulfite), and, among them, glutathione and sodium metabisulfite are preferable.

The sequestering agents are exemplified by ethylenediaminetetraacetic acid, disodium ethylenediaminetetraacetate (EDTA.2Na), disodium calcium ethylenediaminetetraacetate (EDTA.2Na.Ca) and nitrilotriacetic acid, and among them, EDTA.2Na and EDTA.2Na.Ca are preferable.

The amount of the compound [1] to be employed for solubilizing itself in water is about 10 to 200 mg/ml, more preferably about 50 to 150 mg/ml. The amount of the salt of salicylic acid or the salt of the bile acid or the total amount of two or more of them to be added is about 0.6 to 20 weight parts relative to one weight part of the compound [1], more preferably about 1 to 4 weight parts, most preferably 1 weight part.

Solubilization of the compound [1] can be performed by first dissolving or suspending the compound [1] in water, then by adding thereto a salt of salicylic acid or/and a salt of a bile acid, or by mixing the compound [1] and a salt of salicylic acid or/and a salt of a bile acid with water simultaneously, but, preferably, a salt of salicylic acid or/and a salt of a bile acid are first dissolved in water, and then the compound [1] is added thereto. When the compound [1], a salt of salicylic acid or a salt of a bile acid is dissolved in water, dissolution may be conducted, upon necessity, under stirring, shaking or heating.

If further required, an additive such as an isotonizing agent, analgesic, preservative or buffering agent may be supplemented.

The injectable solution prepared thus can be used as is by charging a syringe with it, or, upon necessity, by distributing it into vials and subjecting them to lyophilization to give freeze-dried preparations, then by redissolving the preparation in distilled water for injection before use.

The volume of injectable solution to be administered depends on the subjects, symptoms and the amount of the compound [1] to be administered, but usually about 1 to 10 ml is preferable for one dosage to an adult, and, when required, about 100 to 500 ml as instillation.

When stored for a long term, the compound [1] is unstable in its aqueous solution, and it is preferably formulated in lyophilized preparations. Even the lyophilized preparations above cannot be relied upon for stability sufficient for long-time preservation at room temperature (color-change, redissolubility, etc.), and, therefore, the above-mentioned reducing sulfur compound or sequestering agent is preferably added. The amount of reducing sulfur compound or sequestering agent is, relative to one weight part of the compound [1], preferably about 0.01 to 0.1 weight part when, for example, glutathione is employed, about 0.001 to 0.1 weight part when an alkali metal metabisulfite or an alkali metal sulfite is employed, and about 0.01 to 0.1 weight part when a sequestering agent is employed, while taking the stabilizing effect and safety into consideration. If necessary, two or more species of reducing sulfur compounds or/and sequestering agents may be employed.

Reducing sulfur compounds or sequestering agents may be added to the compound [1] and a salt of salicylic acid or/and a salt of a bile acid, and then dissolved in water, but it is preferable that the reducing sulfur compound or sequestering agent is added after the compound [1] is dissolved in water by the aid of a salt of salicylic acid or/and a salt of a bile acid. The addition may be conducted, upon necessity, with stirring, heating or blowing an inert gas (e.g. nitrogen gas) or with supplement of an additive such as an isotonizing agent, analgesic, preservative or buffering agent.

Thus-prepared solution is distributed into vessels and subjected to lyophilization, after which it is redissolved before use in distilled water for injection or, upon necessity, with the addition of physiological saline solution, 5% aqueous solution of sorbitol, etc.

OPERATION OF THE INVENTION

The compound [1] solubilized by the method of this invention can be administered as stable injectable without causing precipitation. Also, the composition of this invention containing a reducing sulfur compound or a sequestering agent can be stored for a long term even at room temperature as well as in a cold place.

WORKING EXAMPLES

The following examples are intended to illustrate this invention in further detail and should by no means be construed as limiting the scope of the invention.

EXAMPLE 1

In 200 ml of distilled water for injection is dissolved 25 g of sodium salicylate. To this solution is added 25 g of the compound [1], and the mixture is stirred to make a solution. Distilled water for injection is added to the solution to make the whole volume 250 ml. The solution is subjected to sterilizing filtration, and then distributed into vials by 2.5 ml each portion. These vials thus charged are subjected to lyophilization to provide injectable preparations.

EXAMPLE 2

In 250 ml of distilled water for injection is dissolved 30 g of sodium deoxycholate. To this solution is added 30 g of the compound [1], and the mixture is stirred to make a solution. Distilled water for injection is added to the solution to make the whole volume 300 ml. The solution is subjected to sterilizing filtration, and then distributed into vials in 3 ml portions to provide injectable preparations.

EXAMPLE 3

In 200 ml of distilled water for injection are dissolved 15 g of sodium salicylate and 10 g of sodium deoxycholate. To this solution is added 25 g of the compound [1], and the mixture is stirred to make a solution. Distilled water for injection is added to the solution to make the whole volume 250 ml. The solution is subjected to sterilizing filtration, and then distributed into ampoules in 2.5 ml portions to provide injectable preparations.

EXAMPLE 4

By the same procedure as in Example 1, excepting use of 25 g of sodium cholate instead of sodium salicylate, injectable preparations are provided.

EXAMPLE 5

By the same procedure as in Example 1, excepting use of 25 g of sodium taurocholate instead of sodium salicylate, injectable preparations are provided.

EXAMPLE 6

By the same procedure as in Example 2, excepting use of 30 g of sodium dehydrocholate instead of sodium deoxycholate, injectable preparations are provided.

EXAMPLE 7

In 200 ml of distilled water for injection were dissolved 50 g of the compound [1] and 50 g of sodium salicylate. To the solution was added 2.5 g of glutathione while blowing thereinto nitrogen gas. The pH was adjusted to 6.0 with 1N HCl, and then distilled water for injection was added to the solution to make the whole volume 400 ml. The solution was subjected to sterilizing filtration, and distributed into vials in 2 ml portions. These vials were subjected to lyophilization to provide injectable preparations. After storage of these vials at 50° C. for two months, no color change appeared and no change was observed in redissolubility.

EXAMPLE 8

By the same procedure as in Example 7, excepting use of 0.5 g of sodium metabisulfide in place of glutathione in Example 7, an injectable solution of the compound [1] was prepared. The solution was subjected to sterilizing filtration, and distributed into vials by in 2 ml portions, and lyophilized to provide injectable preparations. After storage of these vials at 50° C. for two months, no colorchange appeared and no change was observed in redissolubility.

EXAMPLE 9

In 200 ml of distilled water for injection were dissolved 50 g of the compound [1] and 50 g of sodium deoxycholate. To the solution was added 5 g of EDTA.2Na.Ca while blowing thereinto nitrogen gas. The pH was adjusted to 6.0 with 1N HCl, and then distilled water for injection was added to the solution to make the whole volume 400 ml. The solution was subjected to sterilizing filtration, and distributed into vials in 2 ml portions. These vials were subjected to lyophilization to provide injectable preparations. After storage of these vials at 50° C. for 2 months, no color-change appeared and no change was observed in redissolubility.

EFFECTS OF THE INVENTION

Specific effects of the present invention are described by the following experiments.

EXPERIMENT 1

Various solubilizers were dissolved in water to make the respective concentrations 10% (W/V). To 1 ml each portion of the solutions was added 10 mg of the compound [1], and the mixture was stirred to examine the solubility of the compound [1]. The results are shown in Table 2. Specimens having become clear at room temperature (25° C.) were subjected to similar testing at 5° C.

TABLE 2

| solubilizer | 25° C. | 5° C. |
|---|---|---|
| HCO-50 | X | X |
| TWEEN-20 | X | X |
| TWEEN-40 | X | X |
| TWEEN-60 | X | X |
| PEG-200 | X | X |
| PEG-300 | X | X |
| PEG-400 | X | X |
| PEG-4000 | X | X |
| SPAN-40 | X | X |
| sodium deoxycholate | O | O |
| sodium argininate | X | X |
| guaiacol glycerin ether | X | X |
| monothioglycerol | X | X |
| sodium salicylate | O | O |
| saccharin sodium | O | X |
| nicotinamide | O | X |
| urethane | X | X |
| urea | X | X |
| thiourea | X | X |
| methylacetamide | X | X |
| acetamide | X | X |
| sodium benzoate | X | X |
| sodium acetate | X | X |
| sodium lactate | X | X |
| sodium citrate | X | X |
| sodium isethionate | X | X |
| lactic acid | X | X |
| citric acid | X | X |
| tartaric acid | X | X |
| N—methylglucamine | X | X |
| triethanolamine | X | X |
| monoethanolamine | X | X |
| morpholine | X | X |
| N,N—dimethylacetamide | X | X |
| ethanol | X | X |
| propylene glycol | X | X |
| human serum albumin | X | X |
| taurine | X | X |
| arginine | X | X |
| lysine | X | X |
| histidine | X | X |
| l-methionine | X | X |
| l-threonine | X | X |
| l-cysteine | X | X |
| glycine | X | X |
| l-leucine | X | X |
| l-phenylalanine | X | X |
| l-cystine | X | X |
| l-tryptophan | X | X |
| l-valine | X | X |
| sodium cholate | O | O |
| sodium taurocholate | O | O |
| sodium dehydrocholate | O | O |

O: clear
X: cloudy

EXPERIMENT 2

In distilled water for injection were dissolved 25 g each portion of the compound [1], 25 g each portion of sodium salicylate and a suitable amount of various stabilizers. To respective solutions were adjusted to pH 6.0 with 1N HCl, followed by addition of distilled water for injection to make the whole volume of the respective specimens 200 ml. The specimens were subjected to sterilizing filtration, distributed into vials 2 ml each portion and lyophilized. These vials were stored at 50° C. for one month to examine the stability. The results are shown in Table 3.

TABLE 3

| stabilizer | | 50° C. (One month) | |
|---|---|---|---|
| kind | amount | colorability | redissolubility |
| control | — | + | Δ |
| glutathione | 5.0 | — | O |
| sodium metabisulfite | 0.5 | — | O |
| sodium sulfite | 0.5 | — | O |
| glycine | 5.0 | + | O |
| alanine | 5.0 | + | O |
| glycylglycine | 5.0 | + | O |
| β-alanine | 5.0 | + | O |
| mannitol | 5.0 | + | O |
| thiourea | 5.0 | + | O |
| taurine | 5.0 | + | O |
| sodium ascorbate | 5.0 | ++ | O |
| sodium thioglycolate | 5.0 | + | O |
| EDTA.2Na | 5.0 | — | O |
| EDTA.2Na.Ca | 5.0 | — | O |
| N—(2-mercaptopropionyl)-glycine | 5.0 | + | O |

—: No coloration is observed.
+: Coloration is observed.
++: Remarkable coloration is observed.

Redissolubility was tested by addition of 5 ml each portion of distilled water to each vial.
O : dissolved within one minute
Δ: dissolved within one to three minutes

EXPERIMENT 3

Solubility (at 5° C.) of 50 mg each portion of the compound [1] and compounds analogous thereto in 1 ml of water and in 1 ml of a 5% (W/V) aqueous solution of sodium salicylate was tested. The results are shown in Table 4.

TABLE 4

| | water | aqueous solution of sodium salicylate |
|---|---|---|
| Compound [1] | cloudy | dissolved |
| Compound [2] | clear semi-solid | clear semi-solid |

TABLE 4-continued

| | water | aqueous solution of sodium salicylate |
|---|---|---|
| Compound [3] | clear semi-solid | clear semi-solid |

Compound [2]:
$$\begin{array}{c} CH_2OC_{18}H_{37} \\ | \\ CHOCH_3 \\ | \quad O \\ | \quad \| \\ CH_2OPOCH_2CH_2N(CH_3)_3 \\ | \\ O^- \end{array} \quad +$$

Compound [3]:
$$\begin{array}{c} CH_2OCONHC_{18}H_{37} \\ | \\ CHOCH_3 \\ | \quad O \\ | \quad \| \\ CH_2OPOCH_2CH_2N(CH_3)_3 \\ | \\ O^- \end{array} \quad +$$

As is apparent from Table 3, combinations of sodium salicylate with the compound [2] and with the compound [3] gave only semi-solid properties unsuitable for intravenous administration.

EXPERIMENT 4

Sodium salicylate was dissolved in water, to which was then added the compound [1]. The mixture was stirred to make a solution. Change of the solution with the lapse of time was observed. The results are shown in Table 5.

TABLE 5

| | (15° C.) | |
|---|---|---|
| Time (h) | A | B |
| 0 | — | — |
| 0.5 | — | — |
| 1 | — | — |
| 3 | — | — |
| 5 | — | — |

—: clear
A: containing 10 mg/ml of the compound [1] and 10 mg/ml of sodium salicylate
B: containing 50 mg/ml of the compound [1] and 50 mg/ml of sodium salicylate As is clear from Table 1 and Table 5, the aqueous solution solely dissolving the compound [1] separated the compound [1] as precipitates after 0.5 hour and became a suspension, but the aqueous solution supplemented with sodium salicylate did not become a suspension even after the lapse of five hours.

What is claimed is:

1. An injectable composition for inhibiting platelet activating factor or preventing shock which comprises a therapeutically effective amount of (1) 3-(n-octadecylcarbamoyloxy)-2-methoxypropyl 2-thiazolioethyl phosphate; and (2) an effective solubilizing amount of a solubilizer selected from the group consisting of an alkali metal salt of salicylic acid and a alkali metal salt of a bile acid; wherein the weight ratio of the phosphate to the solubilizer is in a range of from 1:0.6 to 1:20.

2. A composition according to claim 1, wherein the bile acid is cholic acid, glycocholic acid, taurocholic acid, tauroglycocholic acid, cholanic acid, lilthocholic acid, desoxycholic acid, dehydrocholic acid, or chenodesoxycholic acid.

3. A stable injectable composition for inhibiting platelet activating factor or preventing shock which comprises: (1) a therapeutically effective amount of 3-(N-octadecylcarbamoyloxy)-2-methoxypropyl 2-thiazolioethyl phosphate; (2) an effective solubilizing amount of a solubilizer selected from the group consisting of an alkali metal salt of salicylic acid and an alkali metal salt of a bile acid, wherein the weight ratio of the phosphate to the solubilizer is in a range of from 1:0.6 to 1:20; and (3) an effective stabilizing amount of a reducing sulfur compound selected from the group consisting of glutathione, an alkali metal metabisulfite and an alkali metal sulfite or an effective stabilizing amount of a sequestering compound selected from the group consisting of ethylenediaminetetraacetic acid, disodium ethylenediaminetetraacetate, disodium calcium ethylenediaminetetraacetate, and nitrilotriacetic acid.

4. A stable composition according to claim 3, wherein said solubilizer, (2), is an alkali metal salt of salicylic acid, and said stabilizing compound, (3), is a reducing sulfur compound selected from the group consisting of glutathione, an alkali metal metabisulfite and an alkali metal sulfite.

5. A method of solubilizing 3-(n-octadecylcarbamoyloxy)-2-methoxypropyl 2-thiazolioethyl phosphate in water for preparation of an injection composition which comprises using in combination with said phosphate an effective solubilizing amount of a solubilizer selected from the group consisting of an alkali metal salt of salicylic acid and an alkali metal salt of a bile acid wherein the weight ratio of the phosphate to the solubilizer is in a range of from 1:0.6 to 1:20.

6. A method according to claim 5, wherein the bile acid is cholic acid, glycocholic acid, taurocholic acid, tauroglycocholic acid, cholanic acid, lithocholic acid, desoxycholic acid, dehydrocholic acid, or chenodesoxycholic acid.

7. A method according to claim 5, wherein the alkali metal salt of salicylic acid is sodium salicylate.

* * * * *